United States Patent [19]

Day et al.

[11] Patent Number: 4,824,672

[45] Date of Patent: Apr. 25, 1989

[54] METHOD AND COMPOSITION FOR REDUCING SERUM CHOLESTEROL

[75] Inventors: Charles E. Day, Fulton, Mich.; Eric H. Kuhrts, Santa Barbara, Calif.

[73] Assignee: Hauser-Kuhrts, Inc., Santa Barbara, Calif.

[21] Appl. No.: 871,715

[22] Filed: Jun. 6, 1986

[51] Int. Cl.$^4$ .................. A61K 35/78; A61K 9/22
[52] U.S. Cl. ...................... 424/195.1; 424/468; 514/824; 514/960
[58] Field of Search .................. 424/195.1, 468; 514/824, 960

[56] References Cited

U.S. PATENT DOCUMENTS 3,952,096  4/1976  Godfrey et al. .................. 424/156
4,377,601  3/1983  Dreese et al. .................. 426/472
4,764,374  8/1988  Grimberg ...................... 428/128

FOREIGN PATENT DOCUMENTS 0080673  6/1983  European Pat. Off. ......... 424/195.1

OTHER PUBLICATIONS

Kannel, W. B., Thom, T. J., "Declining Cardiovascular Mortality", *Circulation*, 70:331-336 (1984).
National Institutes of Health Consensus Development Conference on Lowering Blood Cholesterol to Prevent Heart Disease, *JAMA*: 253, No. 14, 2980-2086 (1985).
Dawber, T. R., *The Framingham Study*, Cambridge, MA., Harvard University Press, pp. 1-13 and 121-141, (1980).
Thelle, D. S. et al., "The Tromso Heart Study: Methods and Main Results of the Cross-Sectional Study", *Acta. Med. Scand.*, 200:107-118 (1976).
Ross, R., Glomset, J., "The Pathogenesis of Atherosclerosis", *N. Engl. J. Med.*, 295:369-377, (1976).
Henriksen, T. Mahoney, E. M. Steinberg, D., "Interactions of Plasma Lipoproteins With Endothelial Cells", *Ann. N.Y. Acad. Sci.*, 401:102-116 (1982).
U.S. Department of Health and Human Services: Cardiovascular Primer for the Workplace, NIH Publication No. 81-2210, pp. 1-88, esp. p. 75 (Jan. 1981).
Lipid Research Clinics Program: The Lipid Research Clinics Coronary Primary Prevention Trial Results: I. Reduction in Incidence of Coronary Heart Disease, and II. The Relationship of Reduction in Incidence of Coronary Heart Disease to Cholesterol Lowering, *JAMA*, 251: 351-374 (1984).
Superko, H. R., "Decreasing Blood Cholesterol Levels With a Dietary Additive: An Additional Approach to Diet and Drugs", *Cardiovascular Reviews & Reports*, 6: No. 11, 1253-1265 (Nov. 1985).
Khan, A. R. et al., "Effect of Guar Gum on Blood Lipds", *The American Journal of Clinical Nutrition*, 34:2446-2449 (Nov. 1981).
Mokady, S., "Effect of Dietary Pectin and Algin on Blood Cholesterol Level in Growing Rats Fed a Cholesterol-Free Diet", *Nutr. Metabol.*, 15:290-294 (1973).
Kay, R. M. et al., "Effect of Citrus Pectin on Blood Lipids and Fecal Seroid Excretion in Man", *Am. J. Clin. Nutr.*, 30:171-175 (1977).
Johnson et al., "Effect on Gel-Forming Gums of the Intestinal Unstirred Layer and Sugar Transport in Vitro", *Gut*, 22:398-403 (1981).
Isaksson, G. et al., "In Vitro Inhibition of Pancreatic Enzyme Activities by Dietary Fiber", *Digestion*, 24:54-59 (1982).
Jenkins, D. J. et al., "Effect of Pectin, Guar Gum, and Wheat Fibre on Serum-Cholesterol", *The Lancet*, 1116-1117, (May 17, 1975).
Jenkins, D. J. A., "Dietary Fiber and Other Antinutrients: Metabolic Effects and Therapeutic Implications", *Nutritional Pharmacology*, p. 121, (1981).

*Primary Examiner*—John W. Rollins
*Attorney, Agent, or Firm*—Gordon W. Hueschen

[57] ABSTRACT

An orally administrable composition and method for reducing serum cholesterol levels are disclosed. A pharmaceutical composition comprising a gel-forming fiber such as, for example, guar gum, psyllium seed, pectin, glucomannon, oat and barley and a mineral salt such as, for example, calcium carbonate, magnesium carbonate and potassium carbonate is administered to humans to reduce serum cholesterol levels.

12 Claims, No Drawings

METHOD AND COMPOSITION FOR REDUCING SERUM CHOLESTEROL

BACKGROUND OF THE INVENTION

1. Field of the Invention

The present invention is directed to orally administrable pharmaceutical compositions and methods for reducing serum cholesterol. More particularly, the present invention is directed to a method for reducing serum cholesterol levels in humans by the oral administration of a pharmaceutical composition containing an effective quantity of guar gum, or other gel-forming fiber, in combination with calcium carbonate or other mineral carbonates. The addition of mineral carbonates to the gel-forming fiber produces enhanced dispersion of the fiber and improves the speed of hydration in the acid environment of the stomach. The formulation according to the present invention results in significant total serum cholesterol (TC) and lowdensity lipoprotein (LDL) reductions when administered to humans according to the recommended dosage regimen.

2. Objects of the Present Invention

It is a principal object of the present invention to provide novel pharmaceutical compositions for oral administration, which compositions are effective in reducing serum cholesterol levels. Additionally, it is a further object of the present invention to provide a pharmaceutical dosage formulation which contains ingredients which facilitate more complete dispersion of active ingredients in the stomach, facilitating more rapid hydration of gel-forming fibers which are then more bio-available for reduction of serum cholesterol levels. It is a further object of the present invention to provide a highly dispersible, non-prescription, gel-forming fiber dietary additive which lowers serum total cholesterol (TC) levels and low density lipoprotein (LDL) levels. Lastly, it is an additional object of the present invention to provide a palatable dosage form containing a gel-forming fiber and mineral carbonate for the reduction of serum cholesterol levels in humans.

SUMMARY OF THE INVENTION

Generally stated, the present invention accomplishes the above-described objectives by providing a method and pharmaceutical composition for the reduction of serum cholesterol levels comprising ingestion of a composition containing an effective quantity of gel-forming fiber and a mineral carbonate to assist in the dispersion and hydration of the gel-forming fiber. The composition can be administered to hypercholesterolemic patients or to individuals desiring to reduce their serum total cholesterol (TC) or low density lipoproteins (LDL) irrespective of a diagnosis of hypercholesterolemia. Doses of 15 grams/day of the subject composition were administered to patients with elevated serum cholesterol levels. Significant reductions in total serum cholesterol (TC) and low density lipoproteins (LDL) were reported.

DETAILED DESCRIPTION OF THE INVENTION

In a broad aspect, the method of the present invention is based upon the surprising discovery that when a gel-forming fiber, such as for example, guar gum, is combined with a mineral carbonate, such as for example, calcium carbonate, dispersion of the fiber in the gastrointestinal fluids is enhanced and the fiber is hydrated more rapidly and completely. As a result, the dietary fiber is more bioavailable and capable of rendering its cholesterol-reducing effects.

Despite the encouraging recent decline in coronary heart disease (CHD), it remains the number one cause of death in the United States (Kannel, W.B., Thom, T.J., "Declining Cardiovascular Mortality", *Circulation* 70:331–336 (1984)). Coronary heart disease is responsible for over 550,000 deaths in the United States per year. It is responsible for more deaths than all forms of cancer combined. It has been reported that there are more than 5.4 million Americans with sympotomatic coronary heart disease and a large number of others with undiagnosed coronary disease. Over 680,000 hospitalizations resulting from myocardial infarction occur each year in the U.S. The direct health costs associated with these figures are estimated at $8 billion with total economic costs estimated at more than $60 billion (National Institutes of Health Consensus Development Conference On Lowering Blood Cholesterol To Prevent Heart Disease, *JAMA:* 253, No. 14, 2080–2086 (1985)) (hereinafter, NIH Consensus Conference).

The NIH Consensus Conference panel has concluded that a major cause of coronary artery disease is elevated serum cholesterol. In evaulating whether there is a causal relationship between blood cholesterol levels and coronary heart disease, the panel agreed that while it is clear that an elevated blood cholesterol level is not the only cause of coronary heart disease "[t]he evidence supporting a causal relationship between cholesterol levels and coronary heart disease comes from a wealth of congruent results of genetic, experimental pathologic, epidemiologic and intervention studies. These data establish beyond any reasonable doubt the close relationship between elevated blood cholesterol levels and coronary heart disease." (NIH Consensus Conference, at page 2081.)

While multiple modifiable factors associated with the development of clinical CHD have been identified, including cigarette smoking, high blood pressure, obesity, sedentary lifestyle, and elevated blood cholesterol, severe CHD can result from high blood cholesterol levels in the absence of any other contributory risk factors. (See. Dawber, T.R., *The Framingham Study*, Cambridge, MA, Harvard University (1980), pp. 1–13 and 121–141, and Thelle, D.S. et al., "The Tromso Heart Study: Methods and Main Results of the Cross-Sectional Study." *Acta. Med. Scand.*, 200:107–118 (1976)).

In fact, serum cholesterol concentrations may be one of the most important factors and may play a central role in the atherosclerotic process (Ross, R., Glomset, J., "The Pathogenesis of Atherosclerosis", *N. Engl. J. Med.*, 295:369–377 (1976), and Henriksen, T. Mahoney, E.M. Steinberg, D., "Interactions of Plasma Lipoproteins With Endothelial Cells", *Ann. N.Y. Acad. Sci.*, 401:102–116 (1982)).

The lipids in plasma of major clinical importance are cholesterol and triglycerides. Cholesterol is always present as a major ingredient in atherosclerotic plaque, along with fatty acids esters of cholesterol, phosphatides, neutral fats and dihydrocholesterol. Cholesterol is not miscible with water. To carry it in the blood, it is combined or repackaged with protein. The combination of cholesterol and protein is called a lipoprotein. Very low-density lipoproteins (VLDL or pre-beta-lipoproteins), carry endogenously synthesized triglycerides, which are removed by muscle, heart, adipose tissue, and other sites. Major remnants of VLDL metabolism are low-density lipoproteins (LDL or beta-lipoproteins). LDLs are catabolized at cell membranes, but the major organ sites remain uncertain. It is the LDLs which contain the greatest percentage of cholesterol. These particles, when present in excess in the blood, are deposited in the tissues and form a major part of the build-up in the arterial wall to form atherosclerotic plaque which narrows the channels of the coronary arteries which furnish the major blood supply to the heart muscle. High density lipoproteins (HDL or alpha-lipoproteins) contain phospholipids and cholesterol complexed with apolipoproteins, the bulk of which differ from those found in VLDLs and LDLs. It is the HDLs which contain the greatest amount of protein and the smallest amount of cholesterol and are believed to take cholesterol away from cells and transport it back to the liver for processing or removal. In the postabsorptive state, a total plasma cholesterol concentration of 200 mg/dl is distributed very roughly as follows: VLDL, 10; LDL, 120; and, HDL, 50. Most of the plasma triglycerides above about 50 mg/dl will be found in VLDLs.

There is no absolute definition of hyperlipidemia. For biologic variables, upper limits such as the upper five or ten percent of the distribution within the population are often used, but for plasma cholesterol, these statistical limits are too high to be used clinically. Correlations between the cholesterol concentrations in young men in North America and incidence of premature ischemic heart disease indicate that an increasing risk can be detected with the cholesterol is higher than 220 mg/dl, a value close to the mean for men from 40 to 49 years of age in this population. Extrapolation of similar data from other populations suggest that a cholesterol level at birth averages 60 mg/dl. Within one month the average has risen to about 120 mg/dl and by the first year to 175 mg/dl. A second rise begins in the third decade and continues to about age fifty in men and somewhat later in women. In other populations this cholesterol rise in adulthood is far less prominent. It is therefore not to be considered necessarily physiologic. The age-related increases in cholesterol are associated mainly with the rise in LDL concentrations, the increases in triglycerides with a rise in VLDL. HDL concentrations in women average about 20% higher than in men. Estrogen tends to raise and androgens tend to lower HDL levels. The average serum cholesterol level for middle-aged adults in the U.S. is 215 mg/dl. The U.S. Health and Nutrition Examination Survey (1971-1974) indicates that the prevalence rate of a serum cholesterol level in excess of 260 mg/dl in the American male work force between the ages of 45 and 55 years is approximately 30%. (U.S. Department of Health and Human Services: Cardiovascular Primer for the Workplace, NIH Publication No. 81-2210, pp. 1-88, esp. p. 75 (January, 1981)).

Evidence that actively decreasing LDL content in men with hypercholesterolemia results in a lower incidence of cardiovascular events has been greatly strengthened by the results of the Coronary Primary Prevention Trial-Lipid Research Clinic (LRC). This seven-year, randomized double blind trial conducted with 3,806 men convincingly demonstrated a significant reduction of myocardial infarction (MI) and sudden cardiac death in the group that achieved LDL reduction by means of a moderate diet in combination with cholestyramine, a bile acid-sequestering resin. This investigation further demonstrated at a 25% reduction in total plasma cholesterol (TC) concentration results in a 49% reduction in the frequency of myocardial infarction and sudden cardiac death. (Lipid Research Clinics Program: The Lipid Research Clinics Coronary Primary Prevention Trial Results: I. Reduction in Incidence of Coronary Heart Disease, and II. The Relationship of Reduction in Incidence of Coronary Heart Disease to Cholesterol Lowering, *JAMA*, 251: 351-374 (1984)). Accordingly, every 1% reduction in total cholesterol (TC) levels results in an approximately 2% reduction in risk of myocardial infarction.

The classic approach to cholesterol management has been to employ a two-stage treatment. In the first stage, non-pharmaceutical methods, such as low-fat diets, exercise, weight loss and alteration of environmental factors are employed. The second stage involves administration of medications which alter lipid metabolism. The hygienic methods employed in stage one are often fraught with significant problems. A common difficulty with this hygienic aspect of the classic approach is the effort required on the part of the subject to achieve a substantial reduction in plasma LDL's. Frequently, patient-initiation is resisted and long-term compliance may suffer as patients find it difficult to exercise, modify life-long dietary habits and reduce body weight. Often as a result of inadequate patient compliance with hygienic methods above, pharmacologic medications are employed in part as a result of the relative ease of use and rapid results. However, the pharmacologic methods suffer from significant drawbacks as well. Drug side effects are not at all uncommon, and can in some patients be quite severe. Furthermore, frequently an individual is placed on a multiple drug regimen which can result in significant drug interactions.

As a result of the significant drawbacks associated with pharmacologic treatment of hypercholesterolemia, an approach has been suggested which would bridge the gap between nonpharmaceutical methods and administration of pharmacologic agents to reduce cholesterol. One such suggestion has been to administer cholesterol-reducing dietary additives such as gel-forming plant fibers, to individuals desiring to reduce their cholesterol levels (Superko, H.R., "Decreasing Blood Cholesterol Levels With a Dietary Additive: An Additional Approach to Diet and Drugs," *Cardiovascular Reviews & Reports*, 6: No. 11,1253-1265 (November 1985)). One such plant fiber, guar gum, is obtained from the leguminous Guar plant (Cyamopsis Tetragonoloba) which grows to a height of three to six feet. The Guar plant bears bean-like pods, each of which contains six to nine small rounded seeds. The guar seed is typically composed of 40-46% germ, 38-45% endosperm and 14-16% husk. Guar gum is produced from the endosperm of the guar seed. Chemically, guar gum is a galactomannon storage polysaccharide composed of mannose and galactose groups. It is commercially available from, for example, Henkel Corporation as Supercol® Guar Gum in a variety of powder formulations with different granulations and terminal viscosities. Guar gum is used extensively in the food industry and is recognized as safe by the Food and Drug Administration. Furthermore, guar gum has been shown to reduce serum cholesterol levels in normal and hypercholesterolemic subjects. However, problems such as poor dispersibility have been associated with oral dosage formulations (such as tablets or capsules) of pure guar gum or with other gummy fibers such as psyllium seed, pectin or oat. Furthermore, problems associated with its highly viscous nature have been recognized and have hampered the long-term clinical application of guar gum as a palatable cholesterol-reducing agent (Khan, A.R. et al., "Effect of Guar Gum on Blood Lipids," the *American Journal of Clinical Nutrition,* 34:2446-2449 (November, 1981)). Laboratory experiments on capsule formulations of pure guar gum in gastric simulators, which approximate the conditions present in the stomach, indicate that as the capsule dissolves, and hydration of the gum begins, only the powder around the perimeter of the dosage hydrates or gels leaving an unhydrated inner core of gum. This incomplete dispersion leaves perhaps as much as 30% to 40% of the guar fiber unhydrated.

The mechanism of action of guar gum as a plasma cholesterol-reducing agent is unclear. However, the mode of action appears to be associated with its viscosity. It has been postulated that the viscous guar gum may coat the intestinal mucosa and interfere with adsorption of lipids which may be related to an increase in resistance of the unstirred water layer and limit the intestinal bulk phase diffusion. (See, Mokady, S., "Effect of Dietary Pectin and Algin on Blood Cholesterol Level in Growing Rats Fed a Cholesterol-Free Diet," *Nutr. Metabol.,* 15:290-294 (1973), Kay, R.M. et al., "Effect of Citrus Pectin on Blood Lipids and Fecal Steroid Excretion in Man," *Am. J. Clin. Nutr.,* 30:171-175 (1977).) One study found that the presence of a polysaccharide gum in the fluid film surrounding the villi in rat jejunum increases its viscosity and gives rise to a thickening of the rate-limiting unstirred layer in vitro (Johnson et al., "Effect of Gel-Forming Gums on the Intestinal Unstirred Layer and Sugar Transport in Vitro," *Gut,* 22:398-403 (1981)). Other work on rats revealed an elevation of enzyme activity in the intestine that may be due to a slower rate of enzyme degradation. Human evidence also suggests an in vitro inhibition of pancreatic enzyme activity by dietary fibers. Trypsin, amylase, lipase and phospholipidase activities were reduced in human duodenal juice following exposure to various fibers including guar (Isaksson, G. et al., "In Vitro Inhibition of Pancreatic Enzyme Activities by Dietary Fiber," *Digestion,* 24:54-59 (1982)).

Additional possibilities for the gel forming fiber's mechanism of action may include bile acid sequestration, fat adsorption sites, facilitation of gallbladder emptying and gastrointestinal motility. There has been some speculation that hypercholesterolemic activity may be related to diminished caloric intake following administration of these types of fibers. Upon hydration, the fibers gel and provide a full feeling in the stomach which may contribute to a reduction in dietary intake and weight loss. These effects may contribute to reduced blood sugar and cholesterol levels. However, work on rats has suggested that bile salt loss associated with steatorrhea may be the mechanism by which pectin lowers the serum cholesterol. Certain studies indicate that both guar gum and pectin administration was also associated with greatly increased fat loss in the stool. (Jenkins, D.J. et al., "Effect of Pectin, Guar Gum, and Wheat Fibre on Serum-Cholesterol", The Lancet, 1116-1117, (May 17, 1975)).

In Superko, supra, at page 1257, a compilation of clinical studies on the effects of guar gum on blood lipids in humans was collected. The respective studies indicate that a series of different formulations of guar gum such as granules, crispbread and capsules, were administered in various dosages over treatment durations ranging from one week to four months. The results indicated that total serum cholesterol reduction ranged from a nonstatistically signifcant 3.4% up to as high as 16.6%.

Table I illustrates the significantly greater cholesterol-reducing properties of one of the dosage forms according to the present invention. 15 grams of guar gum and calcium carbonate in a capsule formulation in a 5:1 ratio was administered in three divided doses of 5 grams at mealtime to patients with elevated serum cholesterol levels.

TABLE I

| Patient | Total cholesterol (TC) | Percent Reduction (TC) | Low Density Lipoprotein (LDL) | (LDL) Percent Reduction |
|---|---|---|---|---|
| A. | | | | |
| Baseline | 289 mg/dl | | 165 mg/dl | |
| After 2 wks | 204 mg/dl | 29% | 86 mg/dl | 48% |
| After 4 wks | 209 mg/dl | 28% | 98 mg/dl | 41% |
| B. | | | | |
| Baseline | 283 mg/dl | | 208 mg/dl | |
| After 2 wks | 220 mg/dl | 22% | 157 mg/dl | 25% |
| After 4 wks | 206 mg/dl | 27% | 130 mg/dl | 38% |

Taking into consideration the results of the Lipid Research Clinic (LRC) Program, supra, which demonstrated a 49% reduction in the frequency of myocardial infarction and sudden cardiac death with every 25% reduction in total plasma cholesterol, the significant reductions in cholesterol reported in Table I are encouraging.

It is understood that compositions according to the present invention may contain optional preservatives, sweeteners or flavorants which may provide a more palatable dosage form and assist in long-term patient compliance.

According to the present invention, the gel-forming fiber is preferably selected from the group consisting of guar gum, psyllium seed, pectin, glucomannan, oat and barley, and the mineral salt is preferably selected from the group consisting of calcium carbonate, magnesium carbonate, and potassium carbonate, and the ratio of said gel-forming fiber to said mineral salt is preferably in the range of approximately 3:1 to approximately 10:1.

While applicant does not wish to be bound by any single theory, it is postulated that the formulation according to the present invention is more rapidly dispersed and thereby more available for its cholesterol-reducing effects. It is postulated that the formulation according to the method of the present invention exhibits a physical/chemical interaction whereby the mineral carbonate ions interact with the gel which is formed when the guar gum hydrates. Normally, with pure guar gum fiber, bile acid anions diffuse through the gel. With the formulation according to the present invention, the mineral ions, calcium, magnesium and potassium, precipitate the bile acids entrapping, entangling and enmeshing them. The liver then produces more bile acids. Since the lever uses cholesterol to make bile acids, the cholesterol pool becomes depleted, thereby lowering cholesterol levels. Furthermore, the action of the mineral carbonate causes release of carbon dioxide in the stomach which facilitates the rapid dispersion of the guar formulation thereby causing better, more complete and more rapid hydration of the guar fiber. Additionally, the speed of hydration of the guar fiber is enhanced as a result of the more rapid dispersion. The prior art problems of incomplete hydration with an unhydrated inner core are avoided by the composition according to the present invention.

The present invention may be embodied in other specific forms without departing from the spirit or essential attributes thereof and, accordingly, reference should be made to the appended claims, rather than to the foregoing specification, as indicating the scope of the invention.

I claim:

1. An orally administrable pharmaceutical composition for use in reducing serum cholesterol levels consisting essentially of:
   (a) an effective amount of a gel-forming fiber which exhibits cholesterol reducing activity, and
   (b) an orally ingestible non-toxic mineral salt capable of dissolution in the gastric fluid with release of carbon dioxide.

2. A composition according to claim 1 comprising a flavorant, sweetener or preservative.

3. A composition according to claim 1 wherein said gel-forming fiber is a member selected from the group consisting of guar gum, psyllium seed, pectin, glucomannon, oat and barley.

4. A composition according to claim 1 wherein said mineral salt is a member selected from the group consisting of calcium carbonate, magnesium carbonate and potassium carbonate.

5. A composition according to claim 1 wherein the ratio of said gel-forming fiber to said mineral salt is in the range of approximately 3:1 to approximately 10:1.

6. An orally administrable pharmaceutical composition for use in reducing serum cholesterol levels consisting essentially of an effective amount of a gel-forming fiber selected from the group consisting of guar gum, psyllium seed, pectin, glucomannon, oat and barley, and an orally ingestible non-toxic mineral salt capable of dissolution in the gastrointestinal fluid with release of carbon dioxide.

7. A method for lowering serum cholesterol in humans consisting essentially of administering in an oral dosage unit an effective amount of gel-forming fiber and an orally ingestible non-toxic mineral salt capable of dissolution in human gastric fluid with release of carbon dioxide.

8. The method according to claim 7 wherein said gelforming fiber is a member selected from the group consisting of guar gum, psyllium seed, pectin, glucomannon, oat and barley.

9. The method according to claim 7 wherein said salt is a mineral carbonate a member selected from the group consisting of calcium carbonate, magnesium carbonate, and potassium carbonate.

10. The method according to claim 7 wherein the ratio of said gel-forming fiber to said mineral salt is in the range of approximately 3:1 to approximately 10:1.

11. The method according to claim 7 wherein said oral dosage unit also comprises a flavorant, sweetener or preservative.

12. A method for lowering serum cholesterol consisting essentially of administration in an oral dosage unit, an effective amount of gel-forming fiber selected from a member of the group consisting of guar gum, psyllium seed, pectin, glucomannon, oat and barley and an orally-ingestible, non-toxic mineral carbonate capable of dissolution in human gastric fluid with release of carbon dioxide.

* * * * *

UNITED STATES PATENT AND TRADEMARK OFFICE
CERTIFICATE OF CORRECTION

PATENT NO. : 4,824,672
DATED : April 25, 1989
INVENTOR(S) : Charles E. Day and Eric H. Kuhrts It is certified that error appears in the above-identified patent and that said Letters Patent is hereby corrected as shown below:

Title Page, [56] References Cited, OTHER PUBLICATIONS, the second column, line 17; "Seroid" should read -- Steroid --

Col. 1, line 21; "lowdensity" should read -- low-density --
Col. 2, line 12; "sympotomatic" should read -- symptomatic --
Col. 2, line 25; "evaulating" should read --evaluating--
Col. 3, line 33; "with" should read -- when --
Col. 5, line 49; after "has" insert -- also --
Col. 6, line 5; "signifcant" should read -- significant --
Col. 6, line 61; "lever" should read -- liver --
Col. 7, line 21; after "sweetener" insert a comma -- , --

Col. 8, line 24; after "sweetener" insert a comma -- , --

Signed and Sealed this

Seventeenth Day of October, 1989

*Attest:*

DONALD J. QUIGG

*Attesting Officer*    *Commissioner of Patents and Trademarks*